US008252233B2

(12) United States Patent
Tokieda et al.

(10) Patent No.: US 8,252,233 B2
(45) Date of Patent: Aug. 28, 2012

(54) AUTOMATIC ANALYZER AND SAMPLE-PROCESSING SYSTEM

(75) Inventors: Hitoshi Tokieda, Hitachinaka (JP); Yoshimitsu Takagi, Hitachinaka (JP); Takeshi Shibuya, Hitachinaka (JP); Masashi Akutsu, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 179 days.

(21) Appl. No.: 12/342,162

(22) Filed: Dec. 23, 2008

(65) Prior Publication Data

US 2009/0162247 A1 Jun. 25, 2009

(30) Foreign Application Priority Data

Dec. 25, 2007 (JP) ................................. 2007-331312

(51) Int. Cl.
  *G01N 35/00* (2006.01)
(52) U.S. Cl. .............. 422/65; 422/64; 422/67; 422/300; 436/47; 436/50
(58) Field of Classification Search .................... 422/62, 422/63, 65, 67, 99, 300, 500; 436/43, 47, 436/48, 50, 55
See application file for complete search history.

(56) References Cited

U.S. PATENT DOCUMENTS

| | | | | |
|---|---|---|---|---|
| 6,080,364 A | * | 6/2000 | Mimura et al. | 422/67 |
| 6,290,907 B1 | * | 9/2001 | Takahashi et al. | 422/65 |
| 2005/0075757 A1 | * | 4/2005 | Haas et al. | 422/65 |
| 2005/0196320 A1 | * | 9/2005 | Veiner et al. | 700/245 |

FOREIGN PATENT DOCUMENTS

| | | |
|---|---|---|
| JP | 10-019899 | 1/1998 |
| JP | 10-213586 | 8/1998 |
| JP | 2004-279357 | 10/2004 |

* cited by examiner

*Primary Examiner* — Jill Warden
*Assistant Examiner* — Cedric Chan
(74) *Attorney, Agent, or Firm* — Mattingly & Malur, PC

(57) ABSTRACT

A sample-processing system that improves total system processing efficiency, and reduces a sample-processing time, by establishing a functionally independent relationship between a rack conveyance block with rack supply, conveyance, and recovery functions, and a processing block with sample preprocessing, analysis, and other functions. A buffer unit with random accessibility to multiple racks standing by for processing is combined with each of multiple processing units to form a pair, and the system is constructed to load and unload racks into and from the buffer unit through the rack conveyance block so that one unprocessed rack is loaded into the buffer unit and then upon completion of process steps up to automatic retesting, unloaded from the buffer unit. Functional dependence between any processing unit and a conveyance unit is thus eliminated.

8 Claims, 17 Drawing Sheets

AUTOMATIC ANALYZER AND SAMPLE-PROCESSING SYSTEM

BACKGROUND OF THE INVENTION

1. Field of the Invention

The present invention relates generally to sample-processing systems. More particularly, the invention relates to a sample-processing system suitable for efficient operation of a plurality of analyzers different in functionality and in processing capabilities and interconnected using a conveyor line to convey sample racks.

2. Description of the Related Art

Analytical results on blood plasma, serum, urine, and other biological samples provide large volumes of useful information for diagnosing medical conditions, and there are a large number of conventional techniques relating to analyzers intended for automatic processing of such biological samples.

JP-A-10-19899, for example, discloses a technique on which is based an automatic analyzer that includes a plurality of analytical units each equipped with transfer means for loading a rack into the analytical unit, with transfer means provided independently of the former transfer means in order to unload the rack from the analytical unit, and with discrimination means provided on the upstream side of the analytical unit in order to discriminate a request item for a sample. The analyzer, after judging which of the multiple analytical units is to be used to analyze the sample, assigns a rack-loading instruction to an appropriate analytical module.

Also, JP-A-10-213586 describes an automatic analyzer equipped with a plurality of analytical units along a belt conveyor line, with a rack supply unit at one end of the conveyor line, and with a rack recovery unit at the other end of the conveyor line. A standby unit for causing racks to stand by for processing is further disposed in front of the rack recovery unit so as to allow automatic retesting.

In addition, JP-A-279357 describes an automatic analyzer in which a standby disc for causing racks to stand by for processing is disposed on a rack conveyance route between a rack supply unit and an analytical unit, the standby disc being provided for avoiding congestion on the rack conveyance route and for automatic retesting.

SUMMARY OF THE INVENTION

In the automatic analyzer of JP-A-10-19899, a rack conveyance route is determined before the rack is conveyed to the analytical unit. When analysis by multiple analytical units is required, therefore, since samples will be conveyed in order from the upstream side, if there are a large number of samples to be analyzed on the upstream side, the rack conveyance route will become congested and none of any samples to be analyzed only on the downstream side will be able to move past a sample existing upstream.

In the automatic analyzer of JP-A-10-213586, although a return route is provided to convey racks from the downstream side to the upstream side, when a rack is conveyed to a downstream analytical unit first, it will be absolutely necessary that the rack, before being conveyed to an upstream analytical unit, be returned to the rack supply unit located at the uppermost position of the upstream side. In addition to consuming time, such a conveying sequence will obstruct the processing of the racks supplied from the supply unit.

Additionally, the samples that require automatic retest will be concentrated at the standby unit in front of the recovery unit. In a system configuration with a plurality of analytical units each different in processing rate, therefore, even when a rack is present that contains samples whose analytical results have already been output and which are to undergo retests, an unnecessary waiting time will occur since that rack will be unable to pass a rack that has entered the standby unit earlier. Furthermore, for retesting, the rack will need to be returned to the rack supply unit similarly to the above, so the conveying sequence in this case as well will correspondingly consume time and obstruct the processing of the racks supplied from the supply unit.

In the automatic analyzer of JP-A-279357, although the rack standby unit has circular disc construction and is therefore excellent in random accessibility to racks, a dead space occurs on the disc since the racks themselves are of a general shape close to a rectangle. Also, the dead space in the entire system due to the use of the circular disc is large.

Additionally, in a system configuration with a plurality of analytical units, since the rack is conveyed to a downstream analytical unit through the standby disc, the direction of the rack becomes inverse and the traveling direction of the rack needs to be returned to its original direction in front of the next analytical unit.

An object of the present invention is to provide a sample-processing system optimized in terms of total system process flow by assigning only a rack conveyance function to a rack supply unit, a conveying unit, and a recovery unit, as their intended purpose, and assigning all other characteristic and necessary functions of processing units to each of the processing units.

Among major problems associated with conventional techniques is that the rack conveyance unit has a functional block that the standby unit and other analytical units require.

A system according to the present invention includes a buffer unit that causes a plurality of racks to stand by for processing and has random accessibility to each rack, and the buffer unit is combined with each of multiple processing units to form a pair. The system is also constructed to load/unload each rack into/from the buffer unit. One unprocessed rack is loaded into the buffer unit and then upon completion of process steps up to automatic retesting, the rack is unloaded from the buffer unit. Functional dependence between any processing unit and a rack conveyance unit is thus eliminated.

In addition, if a rack transfer block that uses the buffer unit to transfer racks to and from a rack conveyance block is constructed to be able to access both a feed route and return route of the racks conveyed by the rack conveyance unit, minimizing a conveying distance between processing units allows the system to start the earliest executable process first, without being aware of the layout order of multiple processing units, even when the kind of processing of a particular sample spans the multiple processing units. This, in turn, makes it unnecessary to determine the entire rack conveyance route on the upstream side of the system. In addition, upon completion of processing in one processing unit, loads of other processing units can be confirmed, so the rack can be conveyed to the processing unit whose load is the lightest of all processing unit loads. A processing time of the entire system is reduced as a result.

A sample-processing system optimized in terms of total system process flow can be provided.

DESCRIPTION OF THE PREFERRED EMBODIMENTS

An embodiment of the present invention will be described hereunder.

Figure 1:
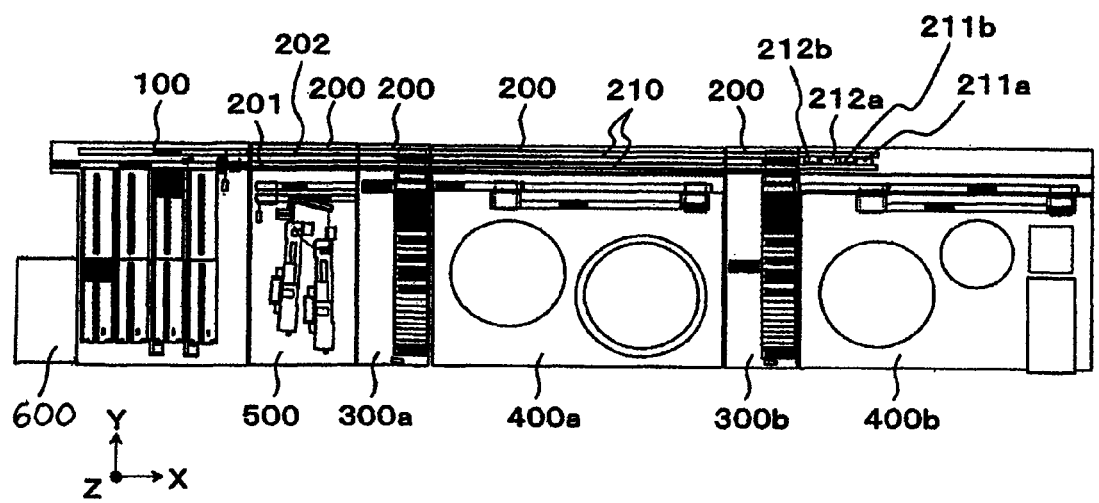
FIG. 1 is a configuration diagram of a sample-processing system according to an embodiment of the present invention.

FIG. 1 is a plan view of a sample-processing system according to an embodiment of the present invention. The system shown as an example in FIG. 1 includes: a sampler unit 100 for loading and storing a sample rack; a rack conveyance unit 200 for conveying the sample rack between the sampler unit and the functional modules; buffer units 300a and 300b each disposed along the rack conveyance unit 200, for transferring the sample rack to and from the rack conveyance unit 200 and for causing temporary standby of the sample rack; functional modules 400a and 400b each paired with the buffer unit 300a or 300b and located to the right thereof; and a supplemental module 500 located to the left of the buffer unit 300a.

Figure 2:
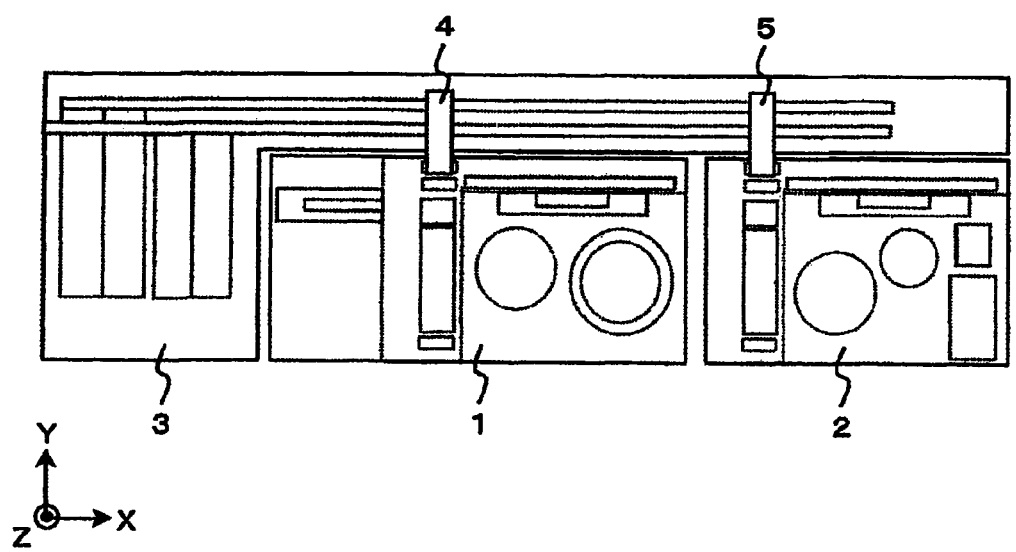
FIG. 2 is a functional block diagram of the system configuration of FIG. 1.

FIG. 2 shows the system of FIG. 1 in functionally classified form. In this case, constituent elements of the system can be classified into a functional block 1 including the buffer unit 300a, the functional module 400a, and the supplemental module 500 in order to undertake sample analysis, preprocessing, and other processes, a functional block 2 including the buffer unit 300b and the functional module 400b, and a sample rack conveyance block 3 including the sampler unit 100 and the rack conveyance unit 200. The functional block 1, the functional block 2, and the conveyance block 3 deliver and receive sample racks to and from each other at connections 4 and 5.

While the functional blocks in the present embodiment are each constructed of a buffer unit and a functional module, a functional module including a buffer unit therein is also embraced in the present invention.

Also, the functional block 1, the functional block 2, and the conveyance block 3 are constructed so that input and output sections required for each will be connected to equipment of related facilities independently of each other. In addition, except for processes relating to the exchange of sample racks between the three blocks, that is, physical movement of each sample rack, issuance of processing requests concerning samples, transmission of results, and exchange of other information, the functional blocks 1, 2 and the conveyance block 3 are constructed to be operable in completely independent form.

Each constituent unit of the system, and total system operation will be described hereunder.

Figure 3:
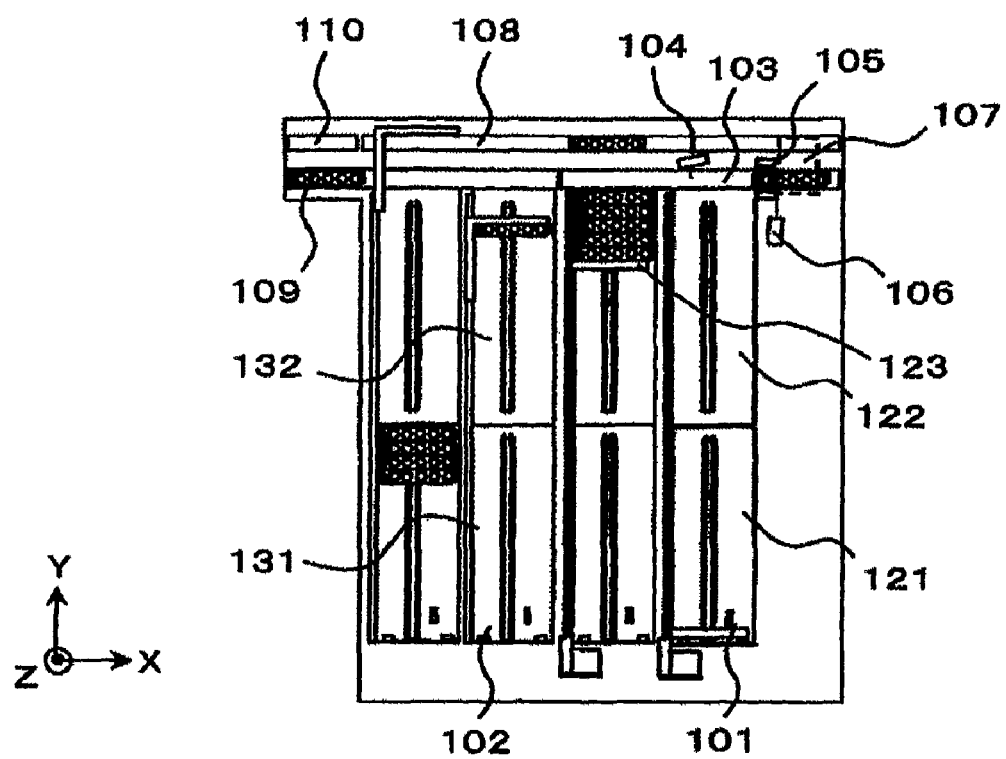
FIG. 3 is a configuration diagram of a sampler unit in the embodiment of the present invention.

A configuration of the sampler unit 100 is shown in FIG. 3.

The sampler unit 100 includes: a loader 101 for loading a sample rack into the system; a storage section 102 for unloading sample racks from the system; a load rack moving unit 103 for transferring a loaded sample rack from the loader to the rack conveyance unit 200; a rack ID reading unit 104 for reading identification (ID) information assigned to the sample rack; a sample vessel height detection unit 105 for confirming whether sample vessels are set up on the sample rack, and detecting the height of each sample vessel; a sample ID reading unit 106 for reading, for example, an ID label of the sample, affixed to the sample vessel set up on the sample rack; a sample vessel rotating unit 107 for rotating the sample vessel during the reading of the sample ID; an unload rack moving unit 108 for moving the rack from the rack conveyance unit 200 to the storage section 102; an emergency-test sample loader 109 for loading an emergency-test sample rack into the sample-processing system or for loading thereinto a sample rack conveyed from a rack conveyance system connected on the upstream side of the sample-processing system; and a rack unloader 110 for unloading the sample rack into the rack conveyance system connected on the upstream side of the sample-processing system.

Figure 4:
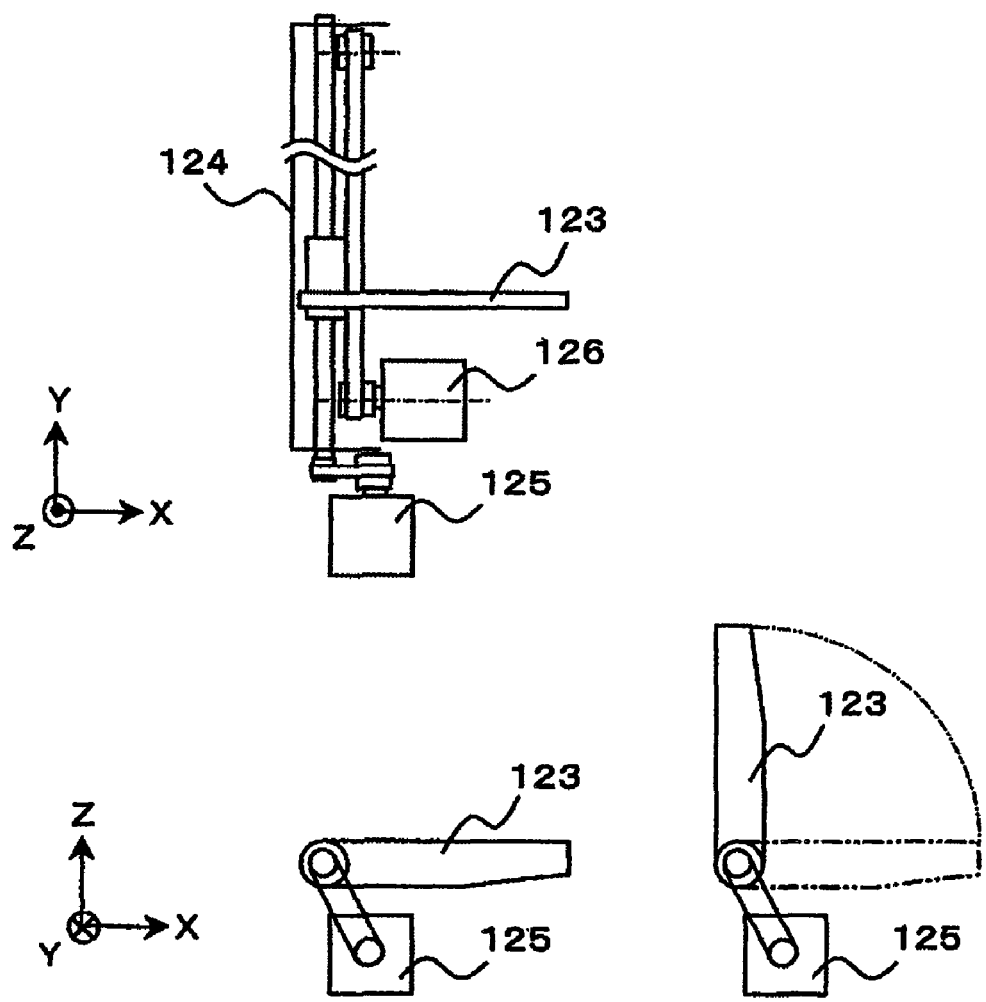
FIG. 4 is a configuration diagram of a load rack-moving mechanism of the sampler unit.

The loader 101 includes a loading tray setup unit 121 in which to set up a sample rack tray capable of being hand-carried with a plurality of sample racks set up thereon, and a loading buffer 122 disposed between the tray setup unit and the load rack moving unit 103. The loader 101 also has a loading lever 123 functioning as a driving mechanism to convey the sample racks in a Y-direction. In addition, the loader 101 has a loading mechanism 124 (see FIG. 4) that is adapted to rotate the loading lever axially in the Y-direction.

After a sample rack tray has been set up in the loading tray setup unit 121, the loading mechanism 124 activates a rotating motor 125 to rotate the loading lever 123, and drives a moving motor 126 to move the sample rack tray in the Y-direction. The sample racks on the tray are thus conveyed to the load rack-moving unit 103 through the loading buffer 122. After all racks have moved out from the loading buffer 122, the loading mechanism 124 rotates the loading lever 123. The lever then returns to a required sample rack tray setup position and stands by for the next sample rack tray to be set up thereat.

Upon completion of the movement of all sample racks from the sample rack tray to the loading buffer 122, the sample rack tray is removable, thus allowing setup of the next sample rack tray. In this case, after moving out all racks from the loading buffer 122, the loading lever 123 of the loading mechanism 124 usually conducts a rack-loading process upon the sample rack tray that has been newly set up in place. Instead, however, the loading process for the sample racks in the loading buffer 122 can be interrupted using a switch (not shown) that is provided on the sampler unit 100, or in accordance with an operator instruction from a screen of an operating unit. After the interruption, the loading lever 123 can be returned to the load tray setup position 121 in order to restart the feed operation for the racks on the sample rack tray.

In addition, the present embodiment has two sample-loading units, and when the rack feed operation by one of the units is completed and all racks are gone from the particular unit, the other unit conducts a rack feed operation. While the present embodiment has two sample-loading units, processing in an arrangement of more than two units also advances similarly.

After receiving the rack from the loading unit, the load rack moving unit 103 transfers the rack to the rack ID reading unit 104, by which the ID of the rack is then read and the rack is further transferred to the sample vessel height detection unit 105.

The sample vessel height detection unit 105 confirms whether sample vessels are set up in internal positions of the sample rack, and detects the height of each sample vessel.

After this, the sample rack is moved to a sample ID reading position, at which the IDs of each sample are then read by the sample ID reading unit 106. A sample-vessel rotating unit 107 is equipped at the sample ID reading position.

In general, bar codes are used as sample IDs. Also, cups, test tubes, test tubes each with a cup thereupon, or other various kinds of objects are used as sample vessels. The bar codes as sample IDs, because of a dimensional requirement for each to have a necessary amount of information, are usually labeled onto test tubes only. During the processing of samples, therefore, whether the sample ID is to be read and whether the sample vessel is to be rotated are judged from the foregoing rack ID information and sample vessel height information.

Necessary processes for the sample rack are determined from the above rack ID and sample ID information. Also, functional modules are determined as conveyance destinations.

After the conveyance destinations of the sample rack have been determined, the load rack-moving unit 103 moves the rack to the rack conveyance unit 200.

An emergency-test sample rack or a sample rack from a sample conveyance system connected on the upstream side of the sampler unit 100 is loaded from the emergency-test sample loader 109 into the sampler unit. The rack that has been loaded from the emergency-test sample loader 109 undergoes substantially the same kind of processing as that of the above-described rack loaded from the sample loader 101, and then moves to the rack conveyance unit 200.

Also, the sample rack that has gone through the necessary processes in each functional module is moved to the storage section 102 by the unload rack moving unit 108.

As with the loader 101, the storage section 102 includes an unloading tray setup unit 131 in which to set up a sample rack tray capable of being hand-carried with a plurality of sample racks set up thereon, and an unloading buffer 132 disposed between the loading tray setup unit and the load rack moving unit 103. An unloading lever 133 for conveying the sample racks in a Y-direction is also equipped as a driving mechanism.

The sample racks that have been conveyed to a front area of the storage section 102 by the unload rack moving unit 108 are conveyed to the unloading buffer 132 through a load rack moving lane by the unloading lever 133, and when the unloading buffer 132 is filled with as many sample racks as mountable on one sample rack tray, the racks are each moved to the tray.

Instead, the sample racks in the unloading buffer 132 can be moved to the sample rack tray in the unloading tray setup unit 131 by operating a switch (not shown) that is provided on the sampler unit 100, or by sending an operator instruction from a screen of an operating unit (not shown).

The sample-processing system further has the rack unloader 110 for unloading a sample rack into the sample conveyance system connected on the upstream side of the sample-processing system. The rack unloader 110 is of a size adapted for holding one rack, and is also constructed to be slidable in a Y-direction so that a position for Y-axial unloading of the rack into the sample conveyance system can be changed.

Figure 5:
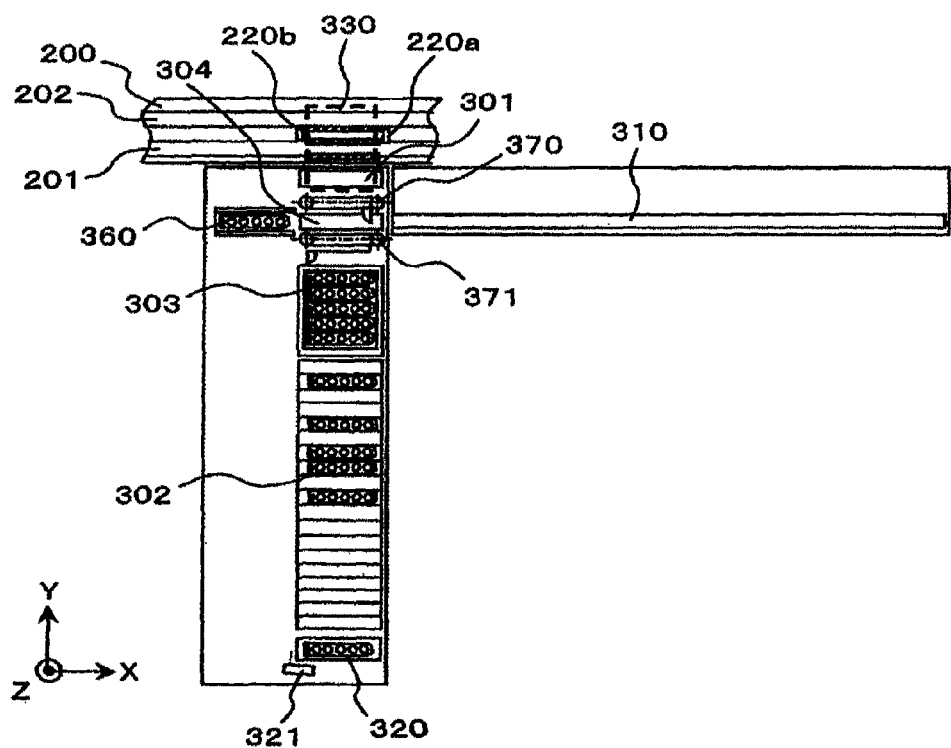
FIG. 5 is a block diagram of a buffer unit in the embodiment of the present invention.
Figure 6:
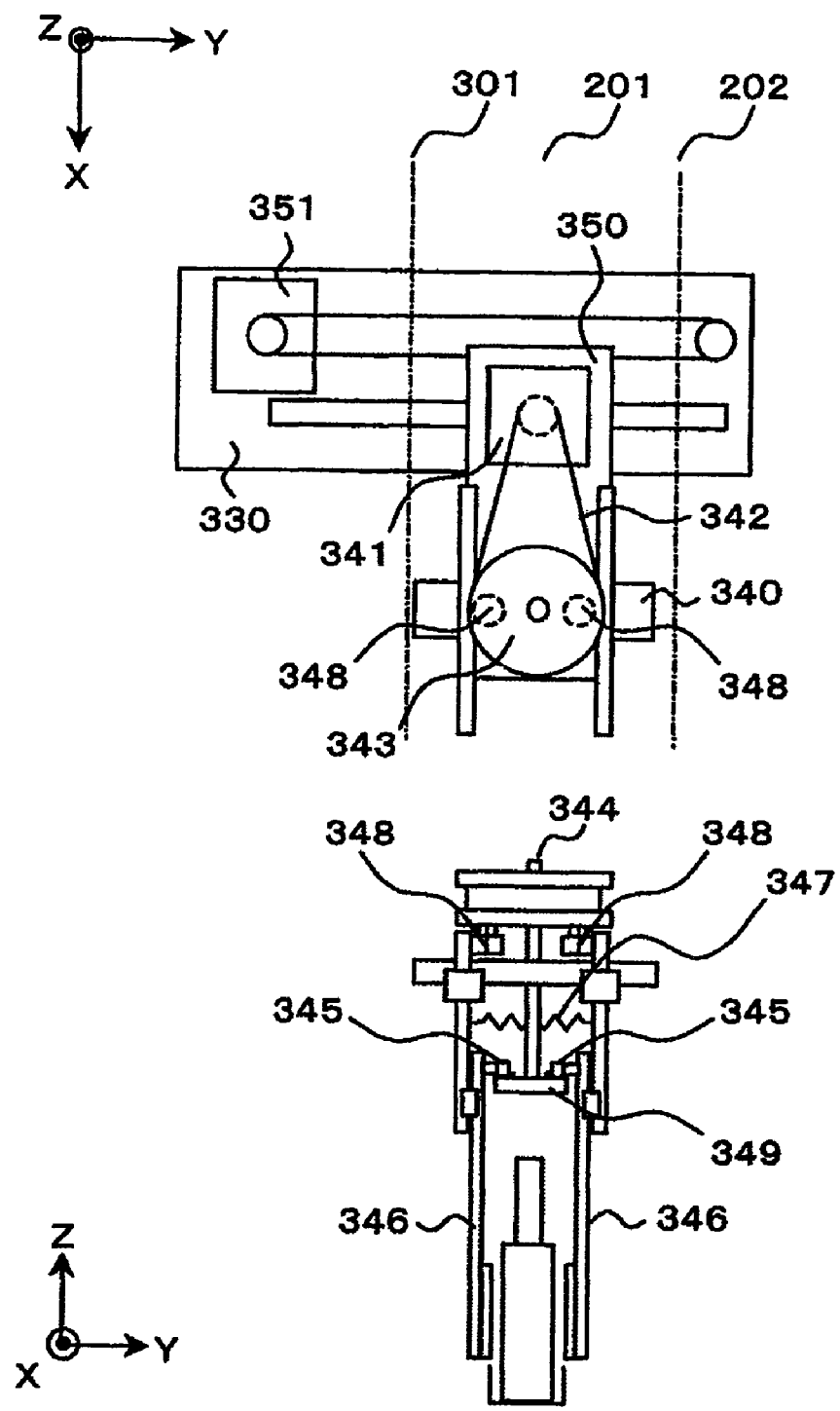
FIG. 6 is a block diagram and operational illustrative diagram showing a rack transfer mechanism of the buffer unit.

The rack conveyance unit 200 in FIG. 1 has two rack conveyance lanes, namely, a feed lane 201 for conveying sample racks from the sampler unit 100 to the functional modules 400a, 400b, and a return lane 202 for conveying the sample racks from the functional modules 400a, 400b to the sampler unit 100. The rack conveyance unit 200 also has a belt mechanism 210, a stopper mechanism 220 (220a and 220b) and a shutter mechanism 230, as shown in FIG. 5.

The belt mechanism 210 uses conveyor belts to convey the sample racks between the sampler unit 100 and the functional modules 400a, 400b, along the feed lane 201 and the return lane 202. In the present embodiment, one conveyor belt is used for the feed lane and the return lane each, and a conveyor belt-driving motor 211 (211a and 211b) and a belt-tensioning mechanism 212 (212a and 212b) are equipped at a terminatory section of the rack conveyance unit 200. This scheme allows rapid sample rack conveyance. Also, this scheme is suitable for a system with a random-conveyance ability to convey sample racks to a plurality of functional modules or bi-directionally between the functional modules arranged on the upstream and downstream sides of the system. Although no description is given in the present embodiment, this scheme may be suitable for a processing system in which, as in a sample preprocessing system, the same sample rack stops at a plurality of functional modules, for example, centrifuging, decapping, and pipetting modules in order from the upstream side of the system to the downstream side to undergo processing. In that case, a plurality of conveyor belts with a length equal to the width of each functional module are arranged in series, and during processing, the sample rack is delivered and received between adjacent conveyor belts. It is desirable, therefore, that an appropriate mechanical configuration of belts be selectable to suit a particular configuration of the system and necessary processing capabilities thereof.

The stopper mechanism 220 for stopping the sample rack at predetermined positions on sample rack loading routes to each functional module has a stopper 220a for the feed lane 201 and a stopper 220b for the return lane 202.

The shutter mechanism 230 has a total of three vertically movable rack guide plates, two for rack guiding on the feed lane 201 and one for rack guiding on the return lane 202, and moves downward only for sample rack unloading into each functional module or for sample rack loading therefrom.

A configuration of a buffer unit 300 is shown in FIG. 5.

The buffer unit 300 including a rack-unloading standby section 301, a buffer 302, a cold-storage section 303, a module loading/unloading standby position 304, a rack conveyance section 310, a one-rack loader/unloader 320, and an ID reader 321, moves the sample rack via rack-unloading mechanisms 370 and 371.

The rack-unloading standby section 301 is a position having a space for causing one rack to stand by, and at this standby position, the sample rack from the rack conveyance unit 200 is transferred to the buffer unit 300. This standby position is also where a sample rack to be unloaded from the buffer unit 300 into the rack conveyance unit 200 is made to stand by.

The buffer 302 further includes a plurality of independent slots in each of which a sample rack can be made to stand by temporarily.

The cold-storage section 303 is constructed so that a plurality of sample racks, each containing accuracy management samples or other samples that require periodic processing in the functional modules, can be made to stand by inside. The cold-storage section 303 has a cold-storage function to prevent these samples from evaporating.

The module loading/unloading standby section 304 is a position having a space for causing one rack to stand by, and at this standby position, the sample rack from the buffer unit 300 is unloaded into the functional module 400. This standby position is also where a sample rack that has undergone processing in the functional module is loaded into the buffer unit 300.

The rack conveyance section 310 conveys the sample rack between the module loading/unloading standby position 304 and the functional module 400.

The one-rack loader/unloader 320 functions as a sample loader/unloader for processing the sample rack in the functional module without involving the rack conveyance unit 200.

A rack transfer mechanism 330 transfers the sample rack bi-directionally in a Y-direction between the rack loading/unloading standby section 301 and the feed lane 201 of the rack conveyance unit 200, and between the rack loading/unloading standby section 301 and the return lane 202. For sample rack transfer in one direction only, the sample rack can usually be moved horizontally if the rack conveyance surface height existing after the rack has been moved is adjusted to be slightly smaller than the rack conveyance surface height existing before the rack is moved. In the present system, however, the transfer mechanism 330 also needs to have a function that lifts the rack in a Z-direction, because bi-directional movement is required and because the rack needs to cross the feed lane 201 to move to and/or from the return lane 202.

The rack transfer mechanism 330 is further detailed below using FIGS. 6 to 10. Rack transfer from the feed lane 201 of the rack conveyance line 200 to the rack loading/unloading standby section 301 is taken as an example in the description.

The rack transfer mechanism 330 includes a gripper 340 and a Y-mover 350. The gripper 340 has a function that opens/closes two gripping plates in a Y-direction to grip the rack, and a function that lifts the gripped rack in a Z-direction. The Y-mover 350 moves the gripper in the Y-direction.

The gripper 340 includes a pulley 343 that transmits driving force using a motor 341 and a belt 342, a rotating shaft 344 of the pulley, two gripping plates 346 fitted with cam followers 345 and movable vertically in the Z-direction, and a spring 347 that works in a direction to draw the gripping plates 346 closer to the spring. Also, the pulley 343 has two bearings 348 and the rotating shaft 344 of the pulley has a stepped cam 349.

The buffer unit 300 activates a driving motor 351 of the Y-mover 350 in the rack transfer mechanism 330, thus moving the gripper 340 to the feed lane 201 of the rack conveyance line 200 in order to load a sample rack. At this time, the gripper 340 is in an open condition, that is, with the two gripping plates 346 pushed open by the two bearings 348 fitted in the pulley 343, and with the cam followers 345 and the cam 349 not in contact with each other.

The rack conveyance unit 200 drives the stopper 220a disposed at the rack transfer position in the buffer unit 300, and protrudes the stopper above the feed lane 201. After this, the rack conveyance unit 200 drives a motor 211a of the belt mechanism 210 and moves the sample rack.

Figure 7:
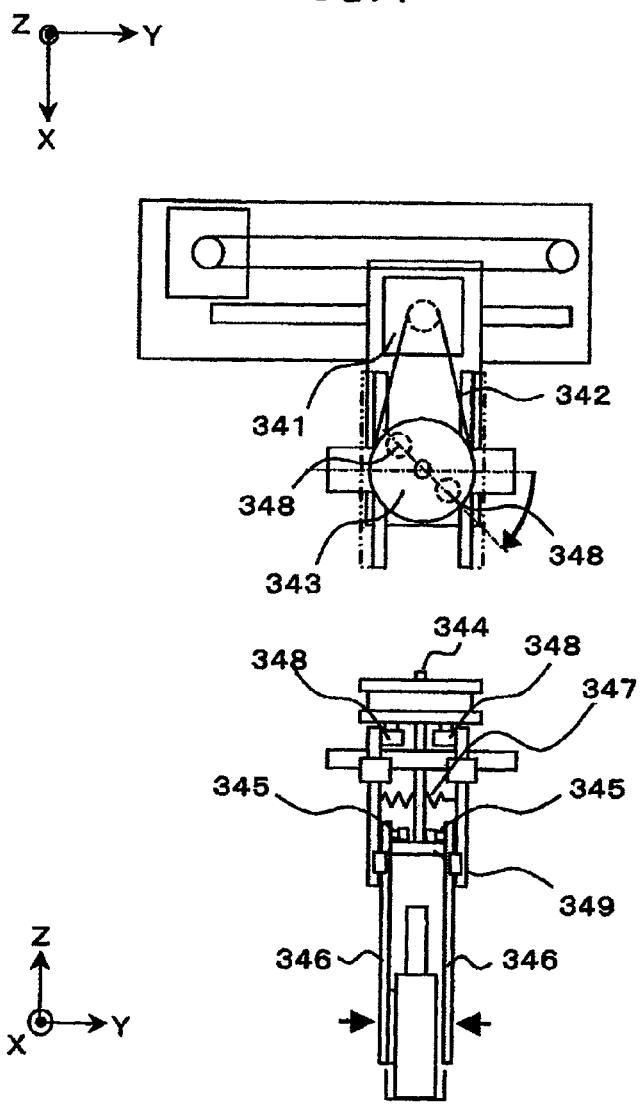
FIG. 7 is another block diagram and operational illustrative diagram showing the rack transfer mechanism of the buffer unit.
Figure 8:
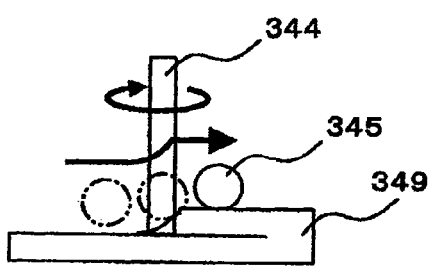
FIG. 8 is yet another block diagram and operational illustrative diagram showing the rack transfer mechanism of the buffer unit.
Figure 9:
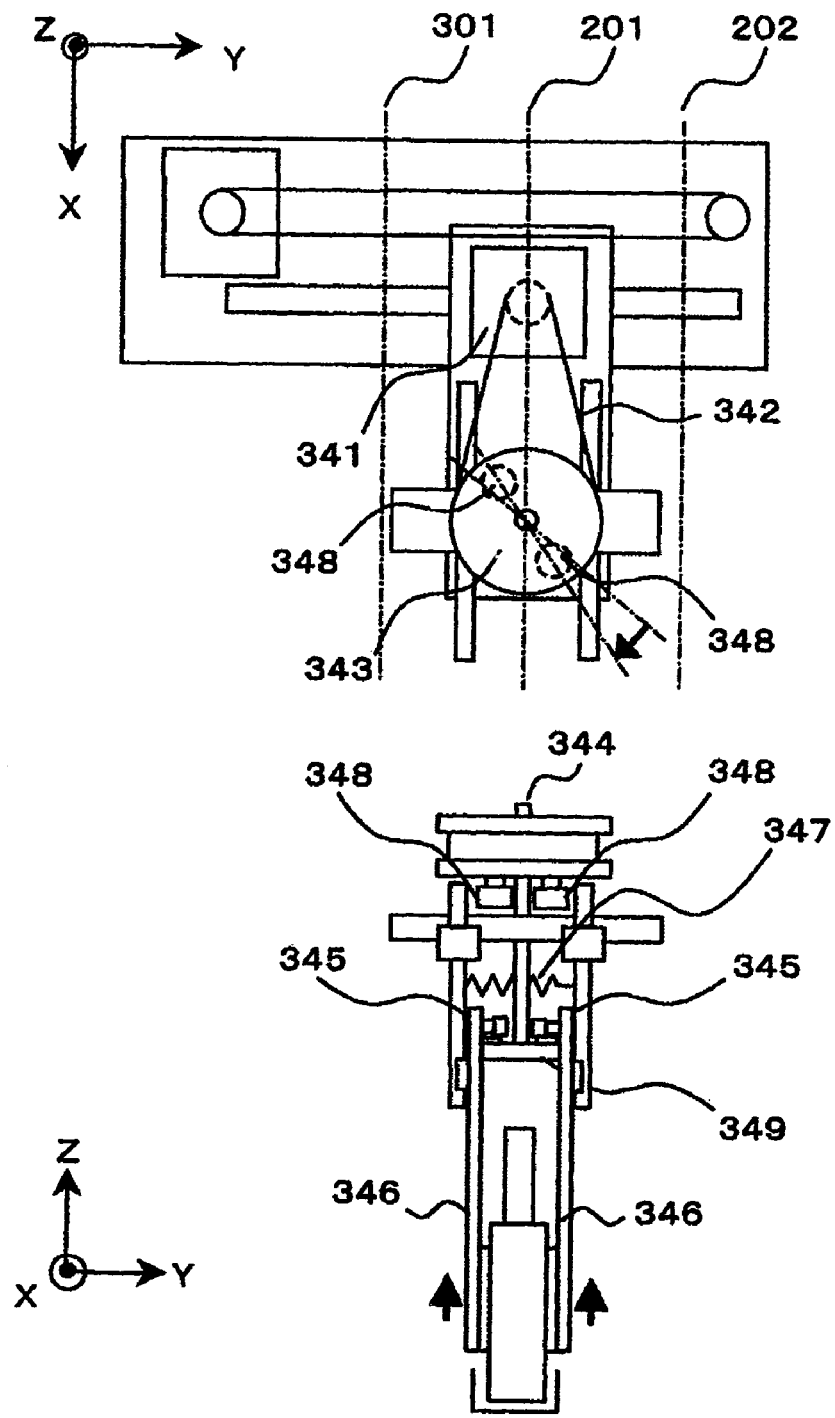
FIG. 9 is a further block diagram and operational illustrative diagram showing the rack transfer mechanism of the buffer unit.
Figure 10:
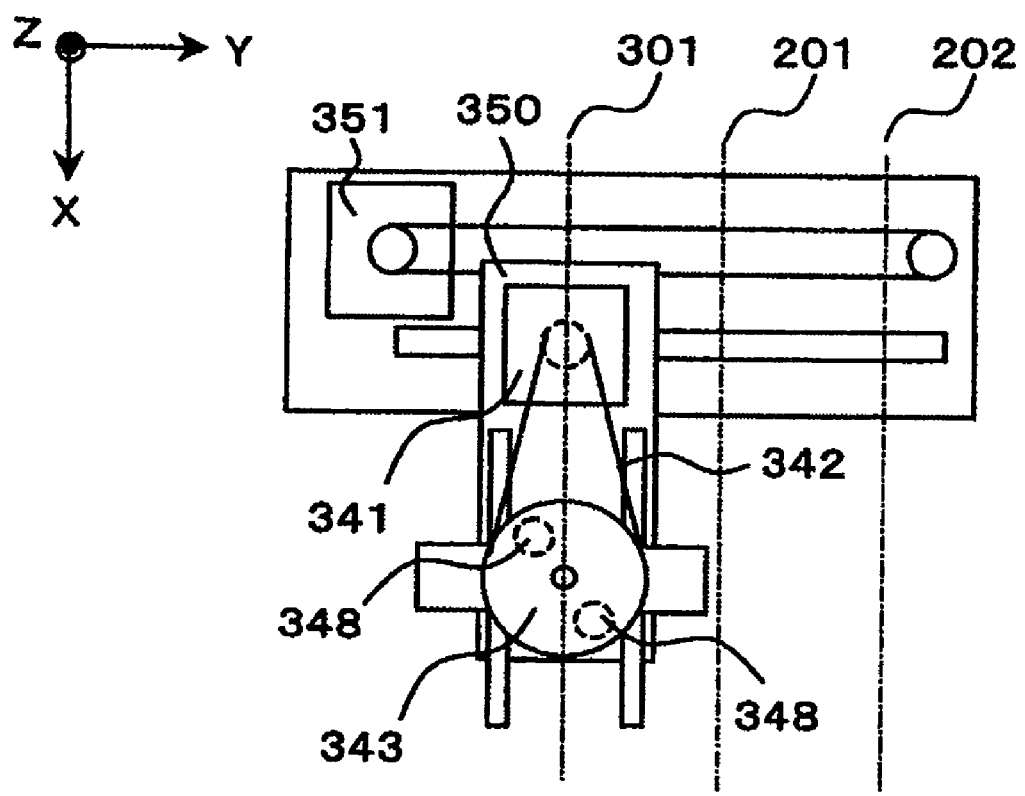
FIG. 10 is a further block diagram and operational illustrative diagram showing the rack transfer mechanism of the buffer unit.

The gripper 340 rotates the pulley 343 by driving the motor 341 to grip the sample rack that has stopped at the transfer position. The rotation of the gripper moves the bearings 348, closes the two gripping plates 346 in the Y-direction by the pulling force of the spring 347, and grips the sample rack, as shown in FIG. 7. Further rotation of the motor 341 brings the bearings 348 into a non-contact state with respect to the gripping plates 346, thus moving the cam followers 345 onto an elevated section of the cam, as shown in FIG. 8, and consequently moving the two gripping plates 346 upward to allow rack lifting in the Z-direction.

After the gripper 340 has lifted the sample rack in the Z-direction, the rack conveyance unit 200 drives a motor of the shutter 230 and moves the shutter 231 downward.

After the shutter 231 has moved downward, the rack transfer mechanism 330 drives the motor 351 of the Y-mover and moves the sample rack in the Y-direction for transfer to the rack loading/unloading standby section 301.

Upon completion of the sample rack transfer, the rack conveyance unit 200 returns the stopper 220a from the feed lane and moves the shutter 230 upward for the next sample rack transfer.

After the movement of the sample rack to the rack loading/unloading standby section 301, the gripper 340 releases the gripped condition of the sample rack. This operation is conducted by rotating the motor 341 in an inverse direction relative to the rotating direction for gripping the rack, and the release is conducted in order reverse to that of gripping.

While the gripper in the present embodiment is constructed to lift the sample rack in operational association with the opening/closing operation of the gripping plates by driving one motor, substantially the same effect can be obtained by providing an independent motor for the gripping plate opening/closing operation and the rack-lifting operation each.

A rack-moving mechanism 360 includes a bucket 361 adapted to hold one rack and move in the Y-direction, an X-mover 362 that moves in the Y-direction with the bucket to move the internal rack thereof in an X-direction, and a vertically movable carriage 363 installed in the X-mover 362.

The rack-moving mechanisms are further detailed below using FIGS. 11 to 14 with the sample rack transfer from the rack loading/unloading standby section 301 to the buffer 302 taken as an example in the description.

Figure 11:
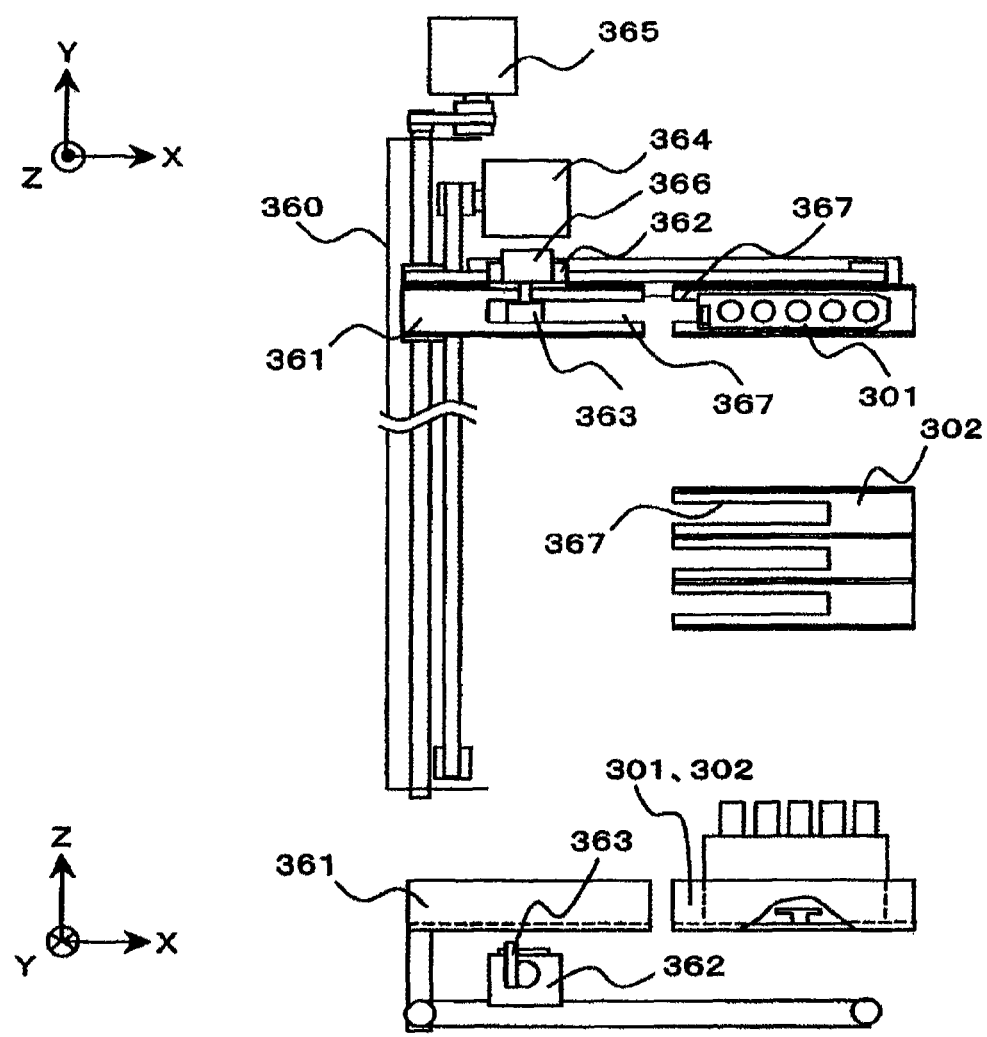
FIG. 11 is a further block diagram and operational illustrative diagram showing the rack transfer mechanism of the buffer unit.
Figure 12:
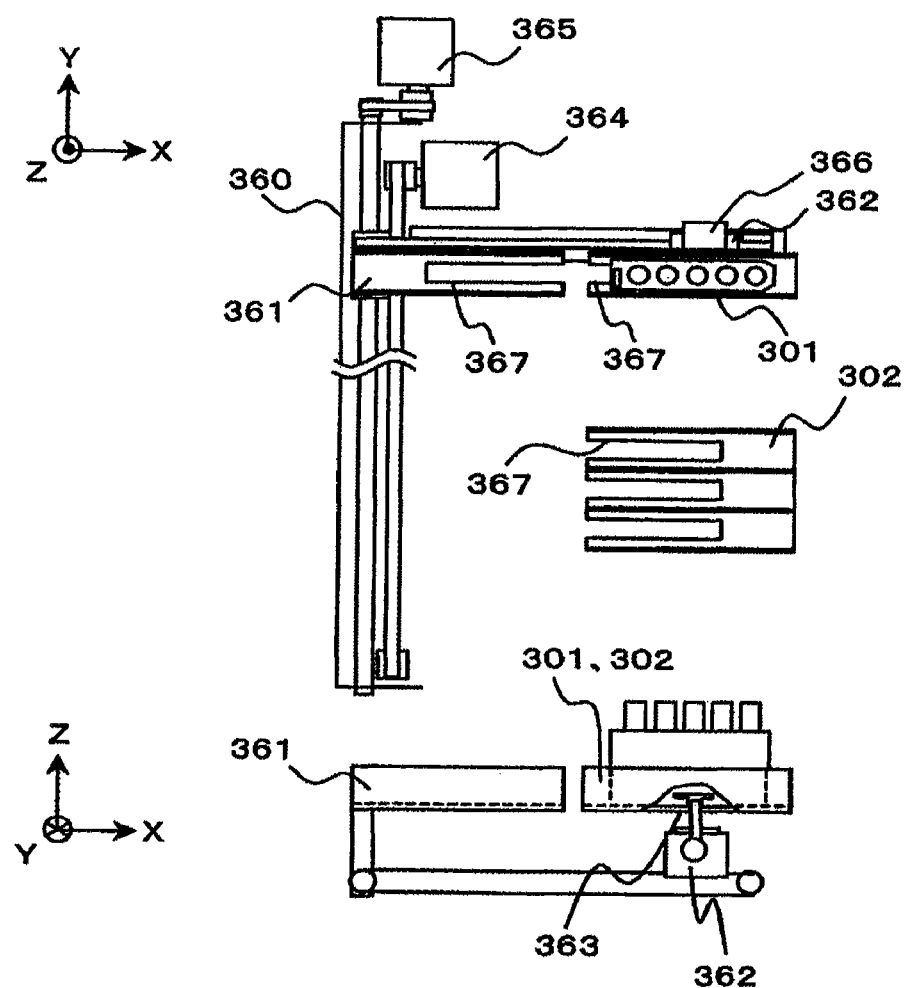
FIG. 12 is a further block diagram and operational illustrative diagram showing the rack transfer mechanism of the buffer unit.

First, the rack-moving mechanism 360 drives a Y-driving motor 364 to move the bucket 361 to the position of the rack loading/unloading standby section 301, as shown in FIG. 11. At the same time, the rack-moving mechanism 360 also drives an X-driving motor 365 to move the carriage 363 of the X-mover 362 to a position under the sample rack in the rack loading/unloading standby section 301, and after the carriage 363 has moved to a position at which the carriage gets into a bottom groove of the sample rack, moves a Z-driving motor 366 to move the carriage upward, as shown in FIG. 12.

The bucket 361 and a sample rack conveyance surface of the rack loading/unloading standby section 301 both have a slit 367 to make the carriage 363 movable in an upward moved condition in the X-direction. A like slit is also provided in the buffer 302, the cold-storage section 303, and other sections using the rack-moving mechanism 360 to move the sample rack.

Figure 13:
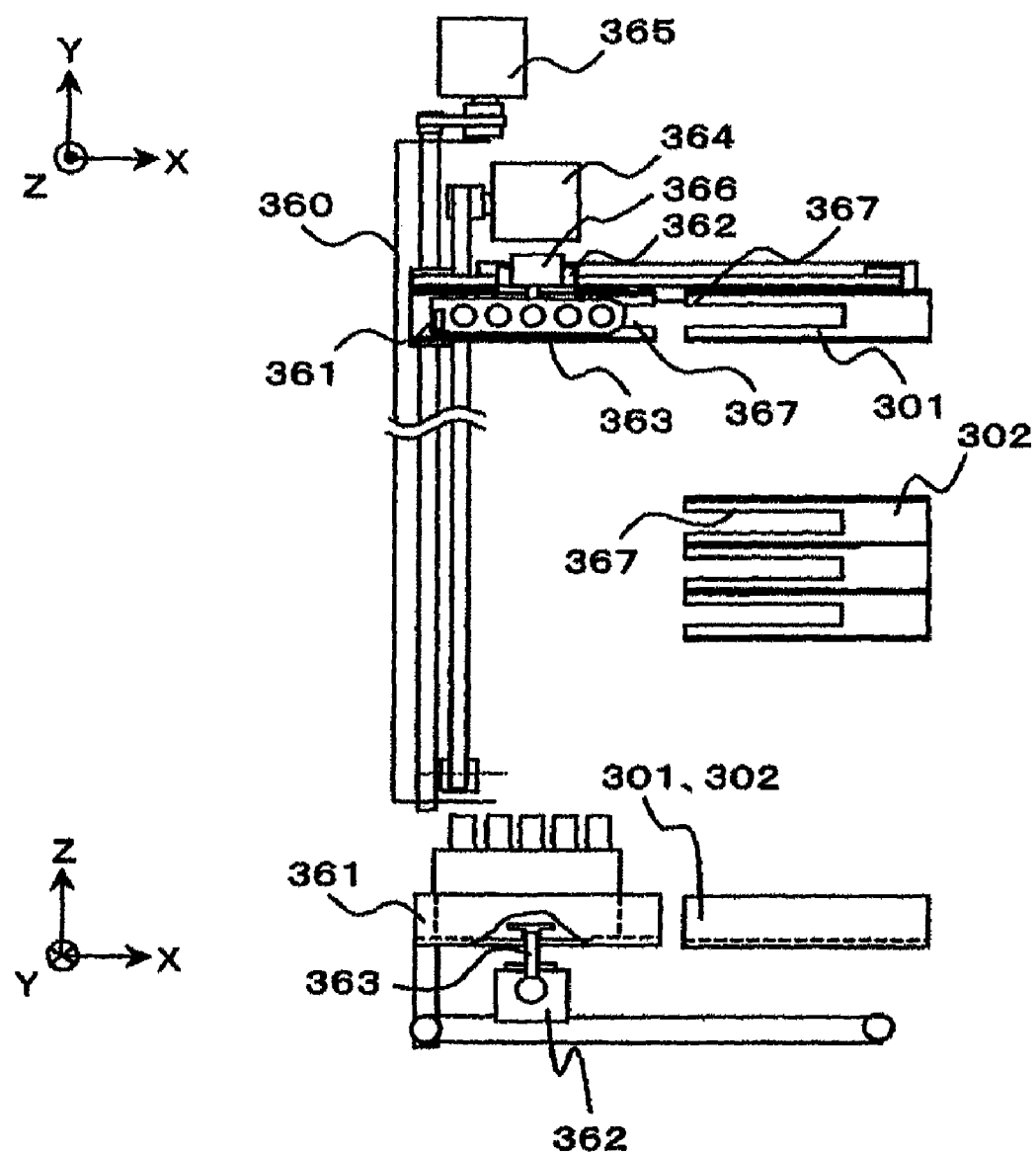
FIG. 13 is a further block diagram and operational illustrative diagram showing the rack transfer mechanism of the buffer unit.

Next, the rack-moving mechanism 360 moves the carriage 363 under the bucket 361 by driving the X-driving motor 365 to move the sample rack to the bucket, as shown in FIG. 13.

After the sample rack has been moved to the bucket 361, the rack-moving mechanism 360 drives the Y-driving motor 364 to move the bucket 361 to a destination slot in the buffer 302. At this time, the carriage 363 remains in an upward position to prevent the rack in the bucket from moving in the X-direction and sliding out from the bucket.

Figure 14:
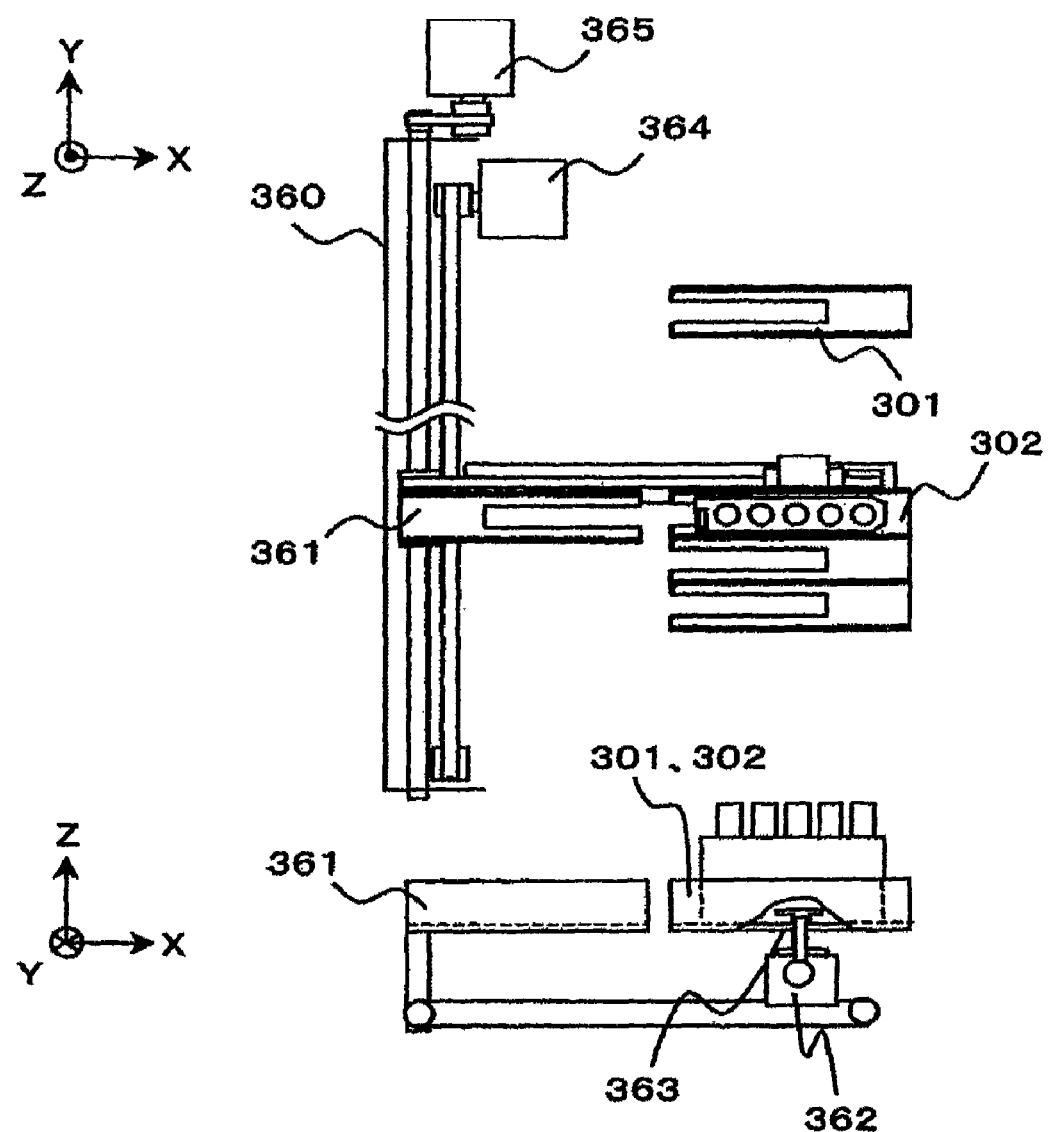
FIG. 14 is a further block diagram and operational illustrative diagram showing the rack transfer mechanism of the buffer unit.

After the bucket has moved to the slot in the buffer 302, the rack-moving mechanism 360 moves the carriage 363 under the slot by driving the X-driving motor 365 to move the sample rack to the slot, as shown in FIG. 14.

In the present embodiment, rack movement from the rack loading/unloading standby section 301 to the bucket 361 has been described. Sample racks are also moved from other sections such as the buffer 302 or cold-storage section 303 to the bucket 361 in essentially the same manner. In addition, while rack movement from the bucket 361 to the buffer 302 has been described, sample racks are moved to the cold-storage section 303, the module loading/unloading standby position 304, and other sections, in essentially the same manner. Constructing other sections so as to have independent standby slots for sample racks allows random accessing of any rack.

Figure 15:
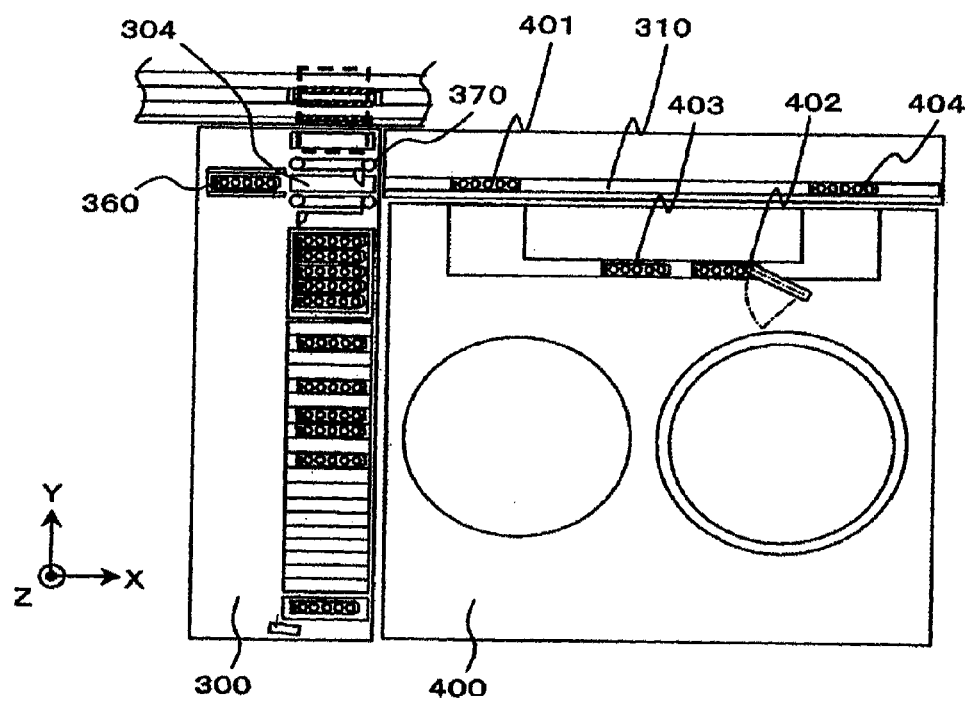
FIG. 15 is an illustrative diagram of rack conveyance between the buffer unit and a functional module.

Next, transferring a sample rack from the buffer unit 300 to the functional module 400 is described below using FIG. 15.

The sample rack transferred to the functional module 400 is moved to the module loading/unloading standby position 304 by the rack-moving mechanism 360, and further moved to the rack conveyance section 310 by the rack-unloading mechanism 370.

The rack conveyance section 310 takes a mechanical configuration suitable for the functional module involved. An example in which the functional module 400 is of a type that draws the sample rack from the rack conveyance section into the functional module and after execution of a necessary process such as pipetting, returns the sample rack to the rack conveyance section, is described in the present embodiment. Also, the functional module in the embodiment has a buffer capable of holding a plurality of racks in series inside.

The sample rack that has been moved to the rack conveyance section 310 by the rack-unloading mechanism 370 is moved on to a sample rack loading position 401 in the functional module by the rack-moving mechanism. The rack-moving mechanism here can be a belt mechanism such as the rack conveyance line 200, or can be a mechanism such as a carriage.

The sample rack that has been drawn into the functional module 400 by a rack-loading mechanism thereof (not shown) is moved to a processing position 402 to undergo the necessary process such as pipetting. During this process, if a following sample rack to be processed in the functional module 400 is present, the buffer unit 300 moves the sample rack to the functional module via the rack conveyance section in essentially the same sequence. The functional module then causes the sample rack to stand by at a buffer position 403 in the module.

After being processed in the functional module 400, the sample rack is once again returned to a rack-unloading position 404 on the rack conveyance section 310 by a rack-unloading mechanism not shown. The rack-moving mechanism moves the sample rack in a direction inverse to that of the transfer of the rack to the functional module 400, thus unloading the rack into the module loading/unloading standby position 304.

In the present embodiment, sample racks move bi-directionally between the buffer unit 300 and the rack conveyance section 310, and rack loading/unloading to/from the buffer unit 300 is controlled according to the number of racks which can be held in the buffer of the functional module 400. In other words, sample rack unloading from the buffer unit 300 is continued until the buffer of the functional module 400 has become full, but after the buffer has become full, the sample rack returned from the functional module 400 will be loaded into the buffer unit 300, so the module loading/unloading standby position 304 is left empty and after the sample rack from the functional module 400 has moved inside the buffer unit 300, the next sample rack is moved to the module loading/unloading standby position 304 and conveyed to the functional module 400 via the rack conveyance section 310.

An example in which the functional module internally has a buffer function to hold a plurality of racks in series with respect to the processing position has been described in the present embodiment. However, essentially the same processing results can be achieved by, for example, using either a functional module of a type to and from which the sample rack can be loaded and unloaded at the same position in the module, or a functional module of a type in which the necessary process such as pipetting can be conducted on the conveyance line without involving rack loading/unloading. In that case, although the mechanical configuration of the rack conveyance section 310 requires a change, there is no need to change the buffer unit 300 or the rack conveyance logic.

Figure 16:
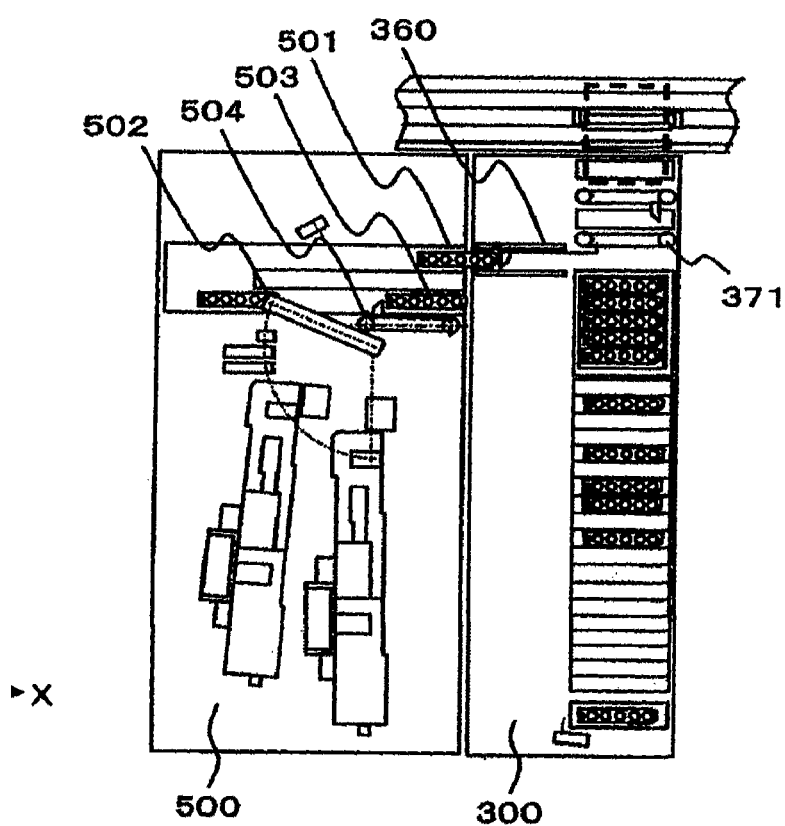
FIG. 16 is an illustrative diagram of rack conveyance between the buffer unit and a supplemental module.

Next, conveying a rack from the buffer unit 300 to the supplemental module 500 is described below using FIG. 16. The supplemental module 500 in the present embodiment is disposed on the left side of the buffer unit 300 and has independent sample rack loading and unloading positions.

A sample rack to be unloaded into the supplemental module 500 is moved to the bucket 361 of the rack-moving mechanism 360, and then further moved to a rack-unloading position 501 in the supplemental module 500 by rotational driving of the Y-driving motor 364 of the rack-moving mechanism 360. After that, the rack-unloading mechanism 371 unloads the sample rack within the bucket 361 onto the conveyance line of the supplemental module by pushing out the rack.

The sample rack that has been carried into the supplemental module is provided with the necessary process, such as pipetting, at the processing position 502 and then moved to a rack unloading standby position 503 on the conveyance line.

At a sample rack unloading request from the rack unloading standby position 503, the rack-moving mechanism 360 of the buffer unit 300 moves the bucket 361 to the rack unloading position 503 in the supplemental module by driving the Y-driving motor 364. A rack-unloading mechanism 504 of the supplemental module moves the sample rack to the bucket 361 after that.

Next, the conveyance of a sample rack which has been loaded from the one-rack loader/unloader 320 is described below.

Upon setup of a sample rack in the one-rack loader/unloader 320 by an operator, the rack-moving mechanism 360 drives the Y-driving motor 364 to move the bucket 361 to the one-rack loading/unloading position 320, and drives the X-driving motor 365 to move the carriage 363 upward to the position of the sample rack. After this, the sample rack is moved to the ID reading unit 372, by which the rack ID is then read. This is followed by movement of the sample rack to a sample vessel detector 373 for sample vessel detection and sample ID reading. Data items of processing in the functional module are determined from the rack ID and sample ID information that has been read. The sample rack that has gone through sample ID reading is moved to the bucket 361, then conveyed to the functional module and the supplemental module in accordance with the above-described conveying sequence, and undergoes processing. The sample rack thus processed is unloaded into the one-rack loader/unloader 320 via the bucket 361 in essentially the same manner as that described above. This completes the conveyance of the rack.

Even if the sampler unit 100 or the rack conveyance line 200 becomes inoperable for reasons such as a failure, processing in the functional module can be achieved by providing a sample rack loader/unloader such as the one-rack loader/unloader 320 shown in the present embodiment, and as described earlier in this Specification, adopting a configuration with independent supply lines for electric power, pure water, and other utilities. In addition, sample racks standing by in the buffer 302 of the buffer unit 300, for example, can be unloaded from the one-rack loader/unloader 320 if the operator sends an unloading instruction from a switch or operating unit not shown.

Next, the cold-storage section 303 in which to make accuracy management samples stand by for processing is described below.

Accuracy management samples are samples whose data measurements are predetermined to verify validity or correctness of the measurement results obtained during analysis with the analyzer. Stability of the apparatus is confirmed by such verification. Accuracy management samples are measured for each of the analytical items periodically, that is, at previously set intervals of time.

After being loaded from the sampler unit 100, a sample rack with accuracy management samples set up therein is transferred to the buffer unit 300 by the rack transfer mechanism 330 thereof. The process flow up to this step is substantially the same as the above.

When the accuracy management sample rack that has been loaded into the buffer unit 300 requires immediate analysis, the sample rack is transferred to the functional module 400 and the samples are analyzed. When immediate analysis is not required or after each sample has been analyzed in the functional module 400, the accuracy management sample rack is conveyed to the cold-storage section 303 for standby.

Since the accuracy management samples have predetermined data measurements as described above, natural evaporation of these samples during prolonged standby in the analyzer causes changes in the data measurements. For this reason, the cold-storage section 303 has a cold-storage function to suppress the evaporation of the samples.

After a fixed time of analysis of a general-test sample, upon an arrival at a time preset to measure an accuracy management sample for a particular item, the accuracy management sample rack standing by in the cold-storage section 303 is conveyed therefrom to the functional module 400 and the accuracy management sample is analyzed. After the analysis, the rack is reconveyed to the cold-storage section 303, in which the rack then waits for a request for measurement of the next accuracy management sample.

The accuracy management sample rack standing by in the cold-storage section 303 is unloaded therefrom under an operator instruction from the operating unit and then stored into the storage section 102 of the buffer unit 100 through the return lane 202 of the rack conveyance unit 200.

Next, total system operation is described below.

Figure 17:
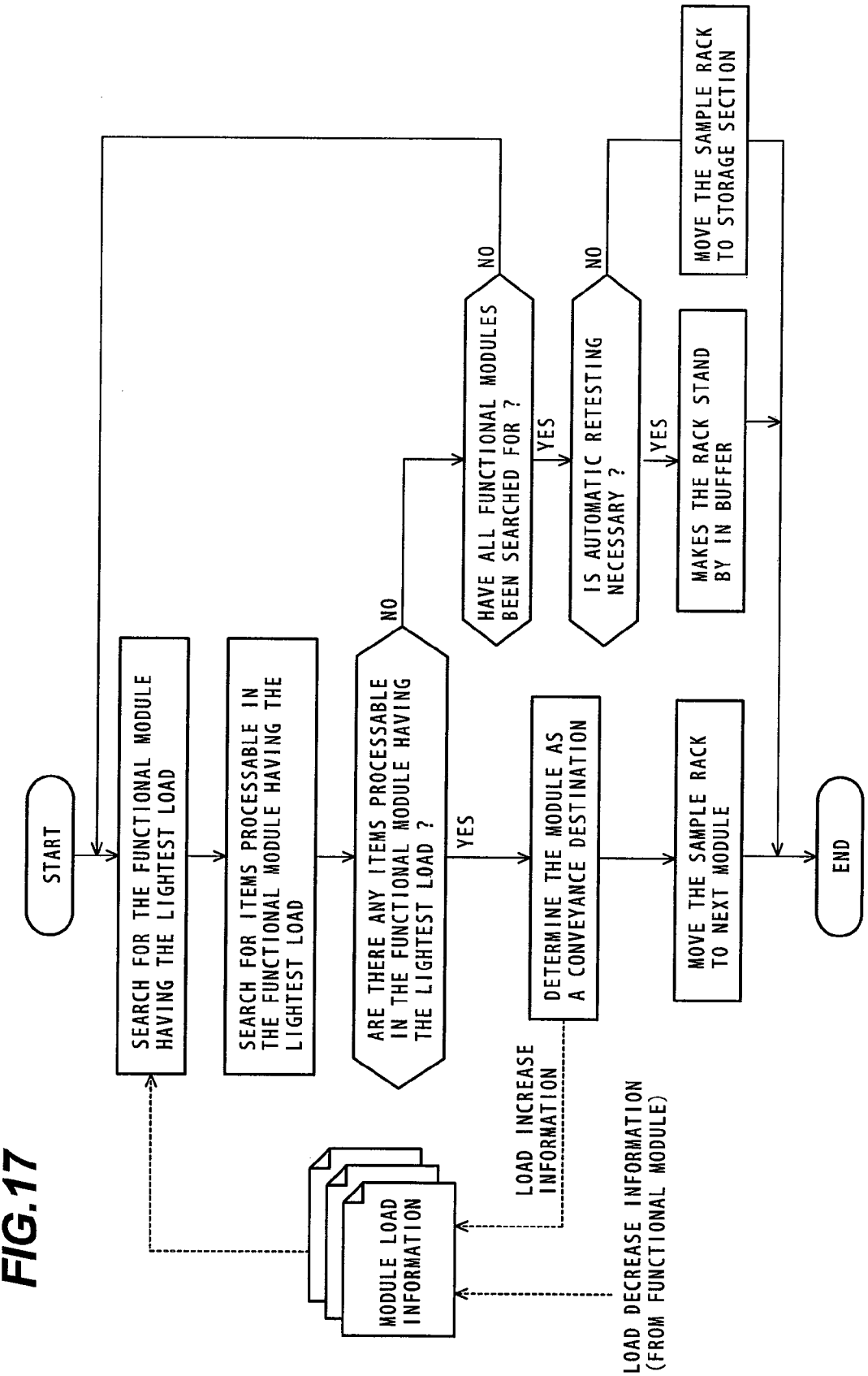
FIG. 17 is a flowchart of rack conveyance route determination.

FIG. 17 is a flowchart showing a method of determining sample rack conveyance routes.

Sample rack conveyance routes are determined upon completion of ID recognition with the rack ID reading unit 104 and sample ID reading unit 106 of the sampler unit 100, upon the unloading of the sample rack into the module rack-unloading position 404 of the buffer unit 300 following completion of processing in the functional module, and upon completion of ID recognition by the ID reader 321 provided to read the sample rack that has been loaded from the one-rack loader/unloader 320.

A system control unit 600 shown in FIG. 1 manages load information on the functional modules that form part of the system, that is, the number of samples and analytical items to undergo processing in each functional module. The system control unit also searches in the above timing for the functional module whose load is the lightest of all module loads. In addition, the system control unit searches for items processable in the functional module. The load here includes processing capabilities of each functional module as well as the number of items to be processed in each functional module, and is based upon, for example, a time up to completion of a preassigned task by the functional module, that is, the time arithmetically derived by multiplying the number of processable items by the time required for execution of the particular process.

The control unit judges whether an extracted functional module can conduct the necessary process for the rack. If the process in the extracted functional module is necessary, this module is determined as a destination to which the rack is to be moved, and the rack is conveyed to the destination.

If, as a result of the module search, a plurality of functional modules identical in load are present and the process for the rack is to be conducted in each of these modules, the functional module nearest to a current position of the rack is determined as the destination thereof.

If the process in the functional module which has been extracted because of the lightest load is unnecessary, the control unit searches for the functional module of the next lowest load, and for items processable in this module, and judges once again whether the necessary process can be conducted for the rack. This sequence is repeated for all functional modules and whether each module can be a destination for the rack.

If none of the functional modules is eventually found to be fit for use as the destination of the rack, the control unit judges whether the rack requires automatic retesting. If automatic retesting is required, the rack is moved to the buffer of the buffer unit and waits for analytical results to be output. After the output of the analytical results, if retesting is necessary, the rack is reconveyed from the buffer to the processing position in the functional module. After being processed, the rack is unloaded from the buffer unit and stored into the storage section of the sampler unit through the return lane of the rack conveyance section. If automatic retesting is unnecessary or if automatic retesting, although it has once been judged to be necessary and the rack has been placed in the buffer for standby, is newly judged from output results not to be necessary, the rack is stored from the buffer unit into the storage section similarly to the above.

Load information on each functional module is updated upon detection of a change in load, that is, upon the determination of a new destination for the sample rack, or upon the unloading thereof into the module rack-unloading position of the buffer unit following an end of the process in the functional module.

Figure 18:
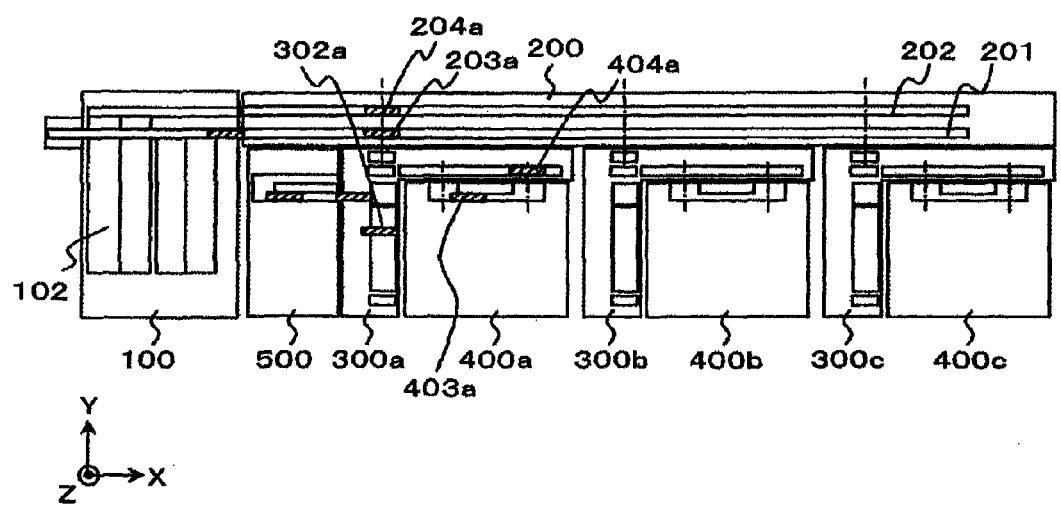
FIG. 18 is an illustrative diagram of the rack flow in the embodiment of the present invention.
Figure 19:
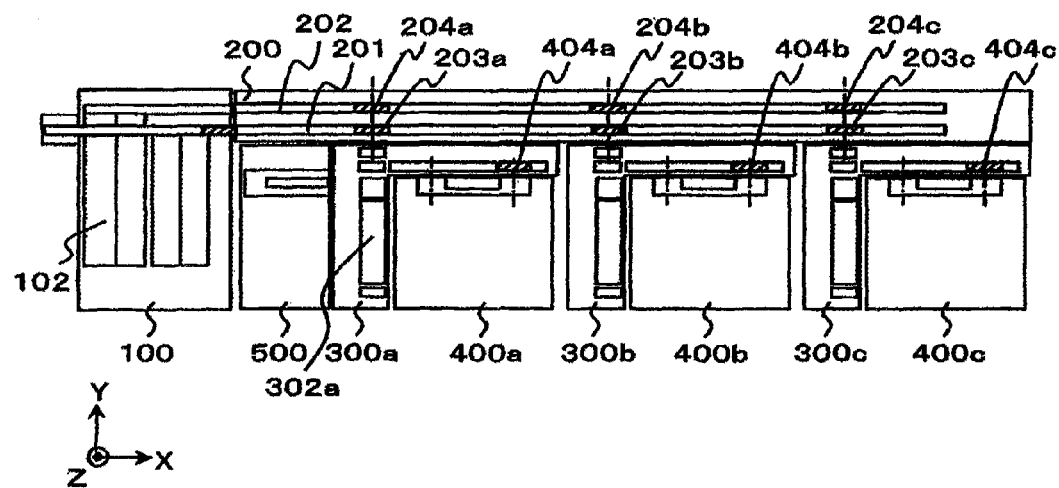
FIG. 19 is another illustrative diagram of the rack flow in the embodiment of the present invention.

Examples of actual sample rack flow are described below. FIGS. 18 and 19 are schematic diagrams of a system which includes a sampler unit 100, a rack conveyance line 200, buffer units 300a, 300b, 300c, functional modules 400a, 400b, 400c, and a supplemental module 500.

A case in which a sample rack requires no processing in the functional module 400a and the supplemental module 500, a load upon the functional module 400a is the lightest of all loads upon the functional modules 400a, 400b, 400c and the supplemental module 500, and automatic retesting is unnecessary, is described as an example below using FIG. 18.

In this case, processing items on the sample rack loaded into the sampler unit 100 are determined from the corresponding rack ID and sample ID information in the same manner as that described above. During the determination, the control unit searches for the functional module with the lightest load, and for items processable in this functional module. The functional module 400a is determined as a conveyance destination since the module 400a is first extracted on the basis of its load information and since the rack requires processing in the module 400a. In accordance with the determination, the sample rack is transferred from a rack loading/unloading position 203a through the feed lane 201 of the rack conveyance unit 200 to the buffer unit 300a.

At this time, if the functional module 400a to which the sample rack has been transferred is ready to immediately process the rack, that is, if an internal buffer 403a of the module 400a is not full, the rack is conveyed to the module 400a. If the functional module 400a is not ready for immediate rack processing, the sample rack is conveyed to a buffer 302a.

After the sample rack has moved to the buffer unit 300a, a conveyance route of the next sample rack loaded from the sampler unit is determined in substantially the same manner as that described above. When the functional module 400a is determined as the conveyance destination of the next sample rack for substantially the same reason as the above, if the total number of sample racks present in and between the buffer unit 300a and functional module 400a or supplemental module 500 on the conveyance route at that time is less than the number of slots in the buffer 302a of the buffer unit 300a, the loading of the next sample rack into the buffer unit 300a is continued and the sample rack is made to stand by in an empty slot of the buffer 302a. If the total number of sample racks is equal to the number of slots in the buffer, the sample rack is made to stand by in the sampler unit until sample rack unloading from the buffer unit 300a into the conveyance unit 200 has been completed.

When a vacancy occurs in the buffer 403a of the module 400a, the sample rack that has been made to stand by in the buffer 302a is conveyed to functional modules, sequentially processed in each of the modules, and unloaded into a module rack-unloading position 404a of the buffer unit 300a. At this point of time, the next conveyance route is determined for the rack. If the loads of the functional module 400b, the supplemental module 500, and the functional module 400c are lighter in that order, the control unit extracts the functional module 400b. However, since the rack requires no processing in 400b, the control unit next extracts the supplemental module 500 whose load is lighter than that of 400b. Since the rack requires processing in the supplemental module 500, this module is determined as the next conveyance destination.

At this time, if the supplemental module 500 is ready for immediate rack processing, the rack is conveyed directly to the supplemental module 500. If the supplemental module is not ready for immediate processing, the sample rack stands by in the buffer 302a and after the supplemental module has become ready, the rack is conveyed to the module.

The rack that has gone through the process in the supplemental module 500 is unloaded into the rack-unloading position 503 thereof. This is followed by the next conveyance routing. Since all necessary processing of the rack is already completed, however, the storage section 102 of the sampler unit 100 is determined as the next conveyance destination. In accordance with the determination, the buffer unit activates the transfer mechanism to move the sample rack to the rack loading/unloading position 204a on the return lane 202 of the rack conveyance unit 200, and then the rack conveyance unit 200 stores the rack into the storage section.

A case in which a sample rack requires processing in the functional modules 400a, 400b, 400c, the load of the functional module 400c is the lightest of all loads upon each functional module and the supplemental module 500, and automatic retesting in the functional module 400b is necessary, is described as another example below using FIG. 19.

In accordance with the flowchart of FIG. 17, the functional module 400c with the lightest load is determined as a first conveyance destination for the sample rack which has been loaded into the sampler unit 100. The loaded sample rack is moved to the rack loading/unloading position 203c, along the feed lane 201 of the rack conveyance unit 200, and after the rack has undergone processing in the functional module 400c via the buffer unit 300c, the next conveyance route is determined at the rack unloading position 404c of the module.

If the loads of the functional modules 400a and 400b at this point of time are the same, the functional module 400b nearest to the functional module 400c is determined as the next conveyance destination of the sample rack. Therefore, the rack is unloaded into a rack loading/unloading position 204c on the return lane 202 of the rack conveyance unit 200 via the buffer unit 300c, then moved to the rack loading/unloading position 204b in the buffer unit 300b through the return lane 202, and processed in the functional module 400b via the buffer unit 300b. After rack processing, the next conveyance route is determined at the rack-unloading position 404b of the module.

If the load of the functional module 400a is the lightest of all module loads at this time, the module 400a is determined as the conveyance destination for the same reason as described above. The rack is unloaded into the rack loading/unloading position 204b on the return lane 202 of the rack conveyance unit 200 via the buffer unit 300b, then moved to the rack loading/unloading position 204a in the buffer unit 300a through the return lane 202, and processed in the functional module 400a via the buffer unit 300a. After rack processing, the next conveyance route is determined at the rack-unloading position 404a of the module.

At this time, a conveyance destination is extracted in accordance with the flowchart of FIG. 17. If, at this time, initial measurement results are already obtained in the functional module 400b and indicate that retesting is necessary, the functional module 400b is determined as the conveyance destination. Conversely if initial measurement results are not obtained and it is unknown whether retesting is necessary, the rack stands by in the buffer 302a of the buffer unit 300a.

If retesting is necessary, the rack is unloaded into the rack loading/unloading position 203a on the feed lane 201 of the rack conveyance unit 200 via the buffer unit 300a, then moved to the rack loading/unloading position 203b in the buffer unit 300b through the feed lane 201, and retested in the functional module 400b. The retesting of the rack is followed by the next conveyance routing at the module rack-unloading position 404b.

At this time, the next conveyance destination is extracted in accordance with the flowchart of FIG. 17. Since all processing required for the rack is already completed, the storage section 102 of the sampler unit 100 is determined as the next conveyance destination. Therefore, the rack is unloaded into the rack loading/unloading position 204b on the return lane 202 of the rack conveyance unit 200 through the buffer unit 300b, and stored into the storage section 102 of the sampler unit 100 through the feed lane 202.

Conversely if retesting is not required, the storage section 102 of the sampler unit 100 is determined as the conveyance destination of the rack which has been standing by in the buffer 302a of the buffer unit 300a. After this, the rack is unloaded into the rack loading/unloading position 204a on the return lane 202 of the rack conveyance unit 200 via the buffer unit 300b, and stored into the storage section 102 of the sampler unit 100 through the feed lane 201.

Figure 20:
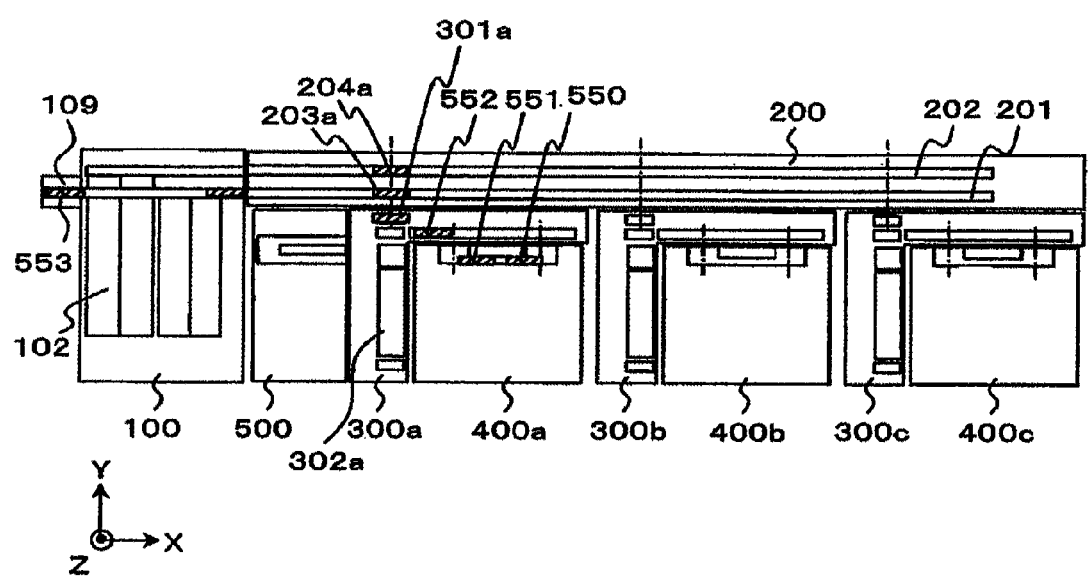
FIG. 20 is an illustrative diagram of emergency-test sample loading rack flow.

Next, process flow relating to a loaded emergency-test sample is described below using FIG. 20. For simplicity, the description assumes that the emergency-test sample requires processing by the functional module 400a only.

The ID of the emergency-test sample rack 553 which has been loaded into the emergency-test sample loader 109 of the sampler unit 100 is read, then the functional module 400a is determined as a conveyance destination, and the rack is loaded from the rack loading/unloading position 203a of the buffer unit 300a into a rack loading/unloading position 301a of the buffer unit 300a. Upon recognizing that the emergency-test sample will soon be loaded, the buffer unit 300a and the functional module 400a start operating to move a general-test sample rack 550, 551, or 552 from the conveyance route to the buffer 302a. When the conveyance route to the functional module 400a becomes useable, the emergency-test sample rack 553 is immediately conveyed thereto for processing. Upon the conveyance of the emergency-test sample rack 553 to the functional module 400a, the general-test sample rack 550, 551, 552 is reconveyed thereto and processing is restarted. The emergency-test sample rack 553 whose processing has ended is stored into the storage section 102 in accordance with the flowchart of FIG. 17.

What is claimed is:

1. A sample-processing system comprising:
   a sample rack conveyance unit;
   a plurality of functional modules positioned along the sample rack conveyance unit, each functional module having a different function to operate as either an analyzer, a preprocessor, or any other device, and each different in processing capability;
   a plurality of buffer units positioned along the sample rack conveyance unit, each buffer unit being combined with any one of the functional modules to form a pair to directly transfer a sample rack between a buffer unit and the functional module combined with the buffer unit;
   the sample rack conveyance unit including a sample rack loader, a first sample rack conveyance section and a sample rack storage section;
   a second sample rack conveyance section conveying a sample rack bi-directionally between a buffer unit and a functional module combined with the buffer unit;
   a rack transfer mechanism for transferring a sample rack bi-directionally between the first sample rack conveyance unit and each buffer unit;
   a plurality of slots arranged in each buffer unit, each of the sample racks standing by in a slot; and
   a sample rack-moving mechanism for loading and unloading a sample rack into and from any one of the slots and for loading and unloading a sample rack to the second sample rack conveyance section.

2. The sample-processing system according to claim 1, wherein an alternative functional module other than the functional module paired with a buffer unit is connected to the other side of the buffer unit which is opposite the side thereof to which the paired functional module is connected.

3. The sample-processing system according to claim 2, wherein the buffer unit includes a mechanism for sample rack loading and unloading between the two functional modules connected to both sides of the buffer unit.

4. The sample-processing system according to claim 1, wherein:
   the sample rack conveyance unit includes a plurality of separate movable sample rack conveyance lanes arranged in parallel to each other; and
   the rack transfer mechanism includes a mechanism for bi-directional transfer of a sample rack from any one of the plural sample rack conveyance lanes to any other thereof, and vice versa.

5. The sample-processing system according to claim 4, wherein:
   the sample rack conveyance unit includes a movable lane for conveying a sample rack in the rightward direction and a movable lane for conveying the sample rack in the leftward direction; and
   the rack transfer mechanism includes a mechanism to load or unload the rack between both lanes.

6. The sample-processing system according to claim 4, wherein the rack transfer mechanism includes a mechanism for gripping the sample rack, and a mechanism for moving the rack; the gripping mechanism using one motor to control both the operation of lifting the rack under the gripped state thereof and the operation of releasing the gripped state after lowering the rack.

7. The sample-processing system according to claim 1, further comprising a control unit configured so that:
   a conveyance destination of the sample rack is determined after reading of ID information of a sample or ID information of the rack or any other identifier, or after pipetting or any other kind of processing by a functional module; and
   a functional module whose operating load is the lightest of all functional module loads is selected as the conveyance destination.

8. The sample-processing system according to claim 1, further comprising a control unit for controlling said sample rack conveyance unit and said rack transfer mechanism, the control unit being configured so that upon loading of an emergency-test sample, the sample rack being processed in the functional module is temporarily moved to one slot in the buffer portion of the buffer unit, then the emergency-test sample is processed preferentially, and after the processing of the emergency-test sample, the sample rack that has been moved to one slot in the buffer portion is reconveyed to the functional module such that the processing of the rack will be restarted.

* * * * *